United States Patent [19]
Bok et al.

[11] Patent Number: 6,096,364
[45] Date of Patent: Aug. 1, 2000

[54] METHOD FOR LOWERING BLOOD GLUCOSE LEVEL BY THE ADMINISTRATION OF BIOFLAVONOID

[75] Inventors: Song-Hae Bok; Tae-Sook Jeong; Ki-Hwan Bae, all of Daejeon; Yong-Bok Park; Myung-Sook Choi, both of Daegu; Surk-Sik Moon, Gongju-shi; Yong-Kook Kwon, Daejeon; Eun-Sook Lee, Daejeon; Byung-Hwa Hyun, Daejeon; Yang-Kyu Choi, Daejeon; Chul-Ho Lee, Daejeon; Byung-Tae Ahn, Cheongju-shi; Sae-Bom Lee, Daejeon, all of Rep. of Korea

[73] Assignee: Korea Institute of Science & Technology, Seoul, Rep. of Korea

[21] Appl. No.: 09/177,463

[22] Filed: Oct. 22, 1998

[30]  Foreign Application Priority Data

Sep. 15, 1998 [KR] Rep. of Korea ...................... 98-37958

[51] Int. Cl.[7] .................................. A23L 1/29; A23L 2/00
[52] U.S. Cl. .............................. 426/590; 426/2; 426/548; 426/590; 426/615; 426/616; 426/618; 424/195.1; 424/439; 514/866
[58] Field of Search ................................ 426/2, 590, 548, 426/615, 616, 618; 424/439, 195.1; 514/866

[56] References Cited

U.S. PATENT DOCUMENTS 4,705,875 11/1987 Mitchell ..................................... 556/46
5,171,573 12/1992 Suzuki et al. ........................... 426/590

FOREIGN PATENT DOCUMENTS 409187230  7/1997  Japan .

OTHER PUBLICATIONS

Morimitsu et al. Protein Glycation Inhibitors from Thyme. Bioscience, Biotechnology and Biochemistry, 59(11)2018–2021, 1995.

Choi et al. Rutin and Functional Inaredients of Buckwheat and their Variations. Korean Journal of Crop Science 41, 69–73, 1996.

Kreft et al. "Buckwheat Based Products". Getreide, Mehland Brot 52(1) 27–30, 1998.

*Primary Examiner*—Helen Pratt
*Attorney, Agent, or Firm*—Anderson Kill & Olick, PC

[57]  ABSTRACT

A method for lowering the blood glucose level in a mammal comprises administering an effective amount of a hesperetin or naringenin bioflavonoid.

9 Claims, No Drawings

METHOD FOR LOWERING BLOOD GLUCOSE LEVEL BY THE ADMINISTRATION OF BIOFLAVONOID

FIELD OF THE INVENTION

The present invention relates to a method for lowering the blood glucose level in a mammal by administering a bioflavonoid thereto.

BACKGROUND OF THE INVENTION

Hyperglycemia is a common disease that afflicts the adult population in developed countries. Hyperglycemia type I, e.g., insulin-dependent diabetes, can be treated by insulin administration, but more than 90% of hyperglycemia patients suffer from insulin-independent hyperglycemia for which insulin treatment is not effective. Although many drugs have been developed for insulin-independent hyperglycemia patients, they are still ineffective and relatively toxic.

The present inventors have endeavored to develop a non-toxic drug having improved efficacy in lowering the blood glucose level; and have unexpectedly discovered that bioflavonoids exhibit excellent blood glucose level lowering effects.

Hitherto, citrus peel has been discarded or used only for the preparation of an animal fodder or organic fertilizer. Dried citrus peel comprises 50 to 60 wt % of alcohol-insoluble polymers such as pectin, hemicellulose and cellulose; 30 to 50 wt % of alcohol-soluble solid materials(80 wt % thereof consisting of glucose, fructose and sucrose); and small amounts of bioflavonoids, vitamins, limonoids, phenolic compounds and oils. In particular, various bioflavonoids, such as those listed in Table I, are present in the citrus peel(Horowitz, R. M., et al., *J. Org. Chem.*, 25, 2183–2187(1960)). Hesperidin is the major bioflavonoid component found in orange, lemon and tangerine; naringin represents the major bioflavonoid component in grapefruit; and naringin and hesperidin are present in citron in nearly equal amounts.

TABLE I

| Citrus fruit | Bioflavonoids |
|---|---|
| Grapefruit | apigenin, dihydrokaempferol, eriodictyol, hesperetin, hesperidin, isorhamnetin, isosakuranetin, kaempferol, naringenin, naringin, neohesperidin, poncirin, quercetin, rutin |
| Lemon | apigenin, apigenin 7-rutinoside, chrysoeriol, diosmin, eriocitrin, hesperidin, isorhamnetin, limocitrin, limocitrol, luteolin 7-rutinoside, naringin, neohesperidin, poncirin, quercetin |
| Orange | auranetin, hesperidin, isosakuranetin 7-rutinoside, naringin, neohesperidin, nobiletin, rutin, sinensetin, tangeretin, vitexin |
| Tangerine | hesperidin, nobiletin, tangeretin |

It has been reported that the bioflavonoids isolated from citrus peel have anti-oxidative, anti-cancer, anti-viral and blood-pressure lowering activities(Saija, A., et al., *Free Radical Biol. Med.*, 19, 481–486(1995); Matsubara, Y., et al., *Japan Organic Synthesis Chem. Association Journal*, 52, 318–327(1994, Mar.); Galati, E. M., et al., *Farmaco.*, 51(3), 219–221(1996, Mar.); Felicia, V., et al., Nutr. Cancer, 26, 167–181(1996); EP 0352147 A2(1990. 1. 24); and Kaul, T. N., et al., *J. Med. Viol.*, 15, 71–75(1985)).

However, bioflavonoids have never been reported to have blood glucose level lowering activity.

SUMMARY OF THE INVENTION

It is, therefore, a primary object of the present invention to provide a method for lowering the blood glucose level in a mammal.

In accordance with the present invention, there is provided a method for lowering the blood glucose level in a mammal which comprises administering an effective amount of a bioflavonoid of formula(I) or a plant extract containing same thereto:

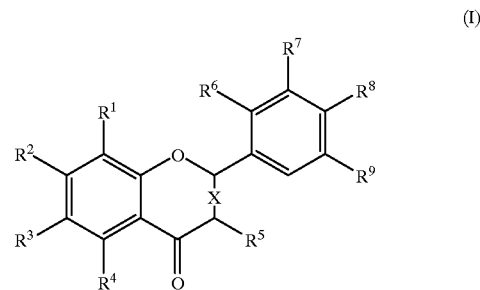

wherein $R^1$, $R^2$, $R^3$, $R^4$, $R^5$, $R^6$, $R^7$, $R^8$ and $R^9$ are each independently hydrogen; a hydroxy group; a $C_{1-9}$ alkoxy group optionally substituted with one or more substituents selected from the group consisting of a hydroxy, $C_{1-5}$ alkoxy, aryloxy, and phenyl group substituted with 1 to 3 substituents selected from the group consisting of a hydroxy, alkoxy, aryloxy, halogen, nitro and amido group; a $C_{5-9}$ cycloalkyloxy group substituted with 1 to 3 substituents selected from the group consisting of a hydroxy, alkoxy, aryloxy, halogen, nitro and amido group; a $C_{5-9}$ cycloalkylcarbonyloxy group substituted with 1 to 3 substituents selected from the group consisting of a hydroxy, alkoxy, aryloxy, halogen, nitro and amido group; a $C_{2-10}$ or $C_{16-18}$ acyloxy group optionally substituted with one or more substituents selected from the group consisting of a hydroxy, $C_{1-5}$ alkoxy, aryloxy, and phenyl group substituted with 1 to 3 substituents selected from the group consisting of a hydroxy, alkoxy, aryloxy, halogen, nitro group; a rutinosyl group; or a rhaminosyl group; and X is a single or double bond.

DETAILED DESCRIPTION OF THE INVENTION

Among the bioflavonoids of the present invention, preferred are those of formula(I) wherein: $R^1$ is H; $R^2$ is OH, a rutinosyl or rhaminosyl group; $R^3$ is H; $R^4$ is OH; $R^5$ is H, OH or a rutinosyl group; $R^6$ is H; $R^7$ is H or OH; $R^8$ is OH or $OCH_3$; and $R^9$ is H.

Particularly preferred bioflavonoids of formula(I) of the present invention are shown in Table II

TABLE II

| | $R^1$ | $R^2$ | $R^3$ | $R^4$ | $R^5$ | $R^6$ | $R^7$ | $R^8$ | $R^9$ | X |
|---|---|---|---|---|---|---|---|---|---|---|
| Eriodictyol | H | OH | H | OH | H | H | OH | OH | H | single bond |
| Hesperidin | H | ORut | H | OH | H | H | OH | OCH$_3$ | H | single bond |
| Hesperetin | H | OH | H | OH | H | H | OH | OCH$_3$ | H | single bond |
| Naringin | H | ORha | H | OH | H | H | H | OH | H | single bond |
| Naringenin | H | OH | H | OH | H | H | H | OH | H | single bond |
| Apigenin | H | OH | H | OH | H | H | H | OH | H | double bond |
| Luteolin | H | OH | H | OH | H | H | OH | OH | H | double bond |
| Diosmin | H | ORut | H | OH | H | H | OH | OCH$_3$ | H | double bond |
| Kaempferol | H | OH | H | OH | OH | H | H | OH | H | double bond |
| Quercetin | H | OH | H | OH | OH | H | OH | OH | H | double bond |
| Rutin | H | OH | H | OH | ORut | H | OH | OH | H | double bond | note) ORut: Rutinosyl group
ORha: Rhaminosyl group

The bioflavonoids of the present invention may be extracted from various plants including vegetables such as lettuce and onion, fruits such as citrus fruit, and grains such as buckwheat, or synthesized in accordance with the conventional process described by Zemplen, Bognar in *Ber.*, 1043(1943) and Seka, Prosche, *Monatsh.*, 69, 284(1936). For example, rutin and quercetin may be extracted from buckwheat by using a suitable solvent such as water or aqueous alcohol under a high temperature and pressure. Alternatively, buckwheat seeds may be allowed to stand overnight in an aqueous solution of Ca(OH)$_2$ or NaOH, and then crude rutin precipitates may be collected after neutralization. Further, dry powders of buckwheat seeds, leaves, stems and flowers may also be used. Generally, the content of rutin in leaves and stems of buckwheat is about 0.6% and that in buckwheat flower is about 3%.

The citrus which can be used in the present invention may be tangerine, orange, lemon, grapefruit and citron. It is preferable to use the peel of citrus fruits uncontaminated by chemical pesticides. The citrus peel extract may be prepared by any of the conventional methods using water or other suitable solvents such as aqueous alcohol, Ca(OH)$_2$ and NaOH.

On the other hand, neohesperidin dihydrochalcone (C$_{28}$H$_{36}$O$_{15}$) of formula(II), which can be easily derived from naringin and has a 1,000 to 1,500 fold higher sweetness than sucrose, may also be used for lowering the blood glucose level:

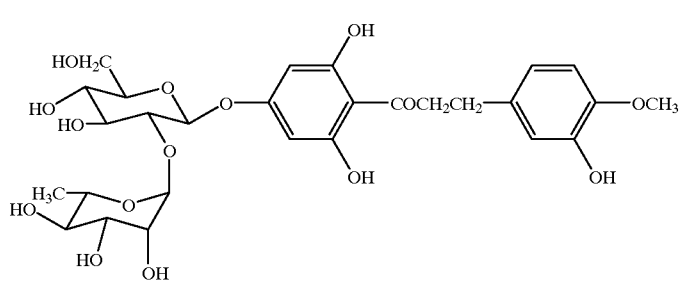

(II)

Bioflavonoids of formulae(I) and (II) starts to exert a blood glucose level lowering effect at a dose of only 0.1 mg/kg/day, the effect increasing with the dose thereof.

Moreover, in spite of their potent efficacies, the bioflavonoid and plant extract containing same show little toxicity or mitogenicity in tests using mice. More specifically, naringin, naringenin, hesperidin, hesperetin, diosmin, neohesperidin dihydrochalcone, quercetin or rutin exhibits no toxicity when it is orally administered to a mouse at a dose of 1,000 mg/kg. Further, the bioflavonoid or plant extract exerts no adverse effects on the liver function.

The present invention also provides a pharmaceutical composition for lowering the blood glucose level, which comprise the bioflavonoid or the plant extract containing same as an active ingredient and pharmaceutically acceptable excipients, carriers or diluents.

A pharmaceutical formulation may be prepared in accordance with any of the conventional procedures. In preparing the formulation, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical composition of the present invention can be administered via various routes including oral, transdermal, subcutaneous, intravenous and intramuscular introduction. In case of human, a typical daily dose of the bioflavonoid may range from about 0.1 to 500 mg/kg body weight, preferably 0.5 to 100 mg/kg body weight, and can be administered in a single dose or in divided doses.

However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Moreover, the bioflavonoid or the plant extract containing same can be incorporated in foods or beverages, as an additive or a dietary supplement, for the purpose of lowering blood glucose level. The foods or beverages may include meats; juices such as a vegetable juice(e.g., carrot juice and tomato juice) and a fruit juice(e.g., orange juice, grape juice, pineapple juice, apple juice and banana juice); chocolates; snacks; confectionery; pizza; foods made from cereal flour such as breads, cakes, crackers, cookies, biscuits, noodles and the likes; gums; dairy products such as milk, cheese, yogurt and ice creams; soups; broths; pastes, ketchups and sauces; teas; alcoholic beverages; carbonated beverages such as Coca-Cola® and Pepsi-Cola®; vitamin complexes; and various health foods.

In this case, the content of the bioflavonoid or the plant extract containing same in a food or beverage may range from 0.01 to 50% by weight, preferably 0.05 to 10% by weight. In particular, the beverage according to the present invention may comprise 200 to 1,000 mg of the bioflavonoid or the plant extract containing same per 1,000 ml of the beverage. In case of plant powder, the content thereof in a food or beverage may range from 0.5 to 10% by weight.

As described above, a bioflavonoid or a plant extract containing same can be used as an effective, non-toxic pharmaceutical agent for lowering the blood glucose level.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1

Toxicity of Orally Administered Rutin 12 seven-week-old, specific pathogen-free ICR female mice, six female mice each weighing about 25 to 29 g and six male mice each weighing about 34 to 38 g, were bred under an environment of 22±1° C., 55±5 % relative humidity and 12L/12D photoperiod. Fodder(Cheiljedang Co., mouse and rat fodder) and water were sterilized and fed to the mice.

Rutin purchased from Aldrich-Sigma Chemical Co.(St. Louis, Mo., U.S.A) was dissolved in 0.5% Tween 80 to a concentration of 100 mg/ml, and the solution was orally administered to the mice in an amount of 0.2 ml per 20 g of mouse body weight. The solution was administered once and the mice were observed for 10 days for signs of adverse effects or death according to the following schedule: 1, 4, 8, and 12 hours after the administration and, every 12 hours thereafter. The weight changes of the mice were recorded every day to examine the effect of citrus peel extract. Further, on the 10th day, the mice were sacrificed and the internal organs were visually examined.

All the mice were alive at day 10 and rutin showed no toxicity at a dose of 1,000 mg/kg. The autopsy revealed that the mice did not develop any pathological abnormality, and no weight loss was observed during the 10 day test period. Accordingly, it was concluded that rutin is not toxic when orally administered to an animal.

EXAMPLE 2

Administration of Bioflavonoids to an Animal 40 three-week-old male Sprague-Dawley rats(Taihan laboratory animal center, Korea) were bred with Lab. chow pellet fodder(Cheiljedang Co.) until the average weight of each rat reached 280 g. Diabetes was induced in the rats by using streptozotocin, which has been known to act specifically on the $\beta$-cell of pancreas and to have no adverse effect on other organs, as follows(see Junod A, et al., *J. Clin. Invest.*, 48, 2129–2139(1969)).

Streptozotocin purchased from Sigma Chemical Co. was dissolved in a citrate buffer(pH 4.5) and the solution was intramuscularly injected to the rats at a dose of 45 mg/kg body weight. The concentration of the streptozotocin solution was controlled so that the maximum injection volume was under 1 ml. 24 hours after the injection, blood samples were taken from tail veins of the rats and the blood glucose level was measured by employing Glucocard II GT-1629 (Kyto Daiichi Kagaku Co., LTP, model 5616239). The blood glucose levels of the rats were within the range from 350 to 400 mg/dl, which demonstrated that diabetes was induced in all of the rats(normal value: 118 mg/dl).

The effect of administering a bioflavonoid to rats on the blood glucose level was determined as follows.

One day after the injection of streptozotocin, the rats were fasted for 6 hours and blood samples were taken from their tail veins to confirm the hyperglycemia of the rats. Then, the rats were divided into four dietary groups (n=10) by a randomized block design.

The rats of the four groups were fed with AIN-76 (American Institute of Nutrition) semipurified diet(control group); and AIN-76 semipurified diet containing 0.05% of naringin(naringin group), 0.05% of hesperidin(hesperidin group) and 0.05% of rutin(rutin group), respectively. The rats were bred for 5 weeks under a constant temperature (25±2° C.), humidity(50±5° C.) and natural illumination while being allowed free access to the diets and water.

At the end of the five week period, the rats were fasted for 12 hours and anesthetized with ether, and then, blood samples were taken from the inferior vena cava. Each of the blood samples was centrifuged at 3,000 rpm at 4° C. for 15 minutes to separate a serum. The blood glucose level of the serum was measured by employing Glucocard II GT-1629 (Kyto Daiichi Kagaku Co., LTP, model 5616239) and the result is shown in Table III.

TABLE III

| Group | Glucose Level (mg/dl) | % Decrease |
| --- | --- | --- |
| Control | 730.50 ± 64.65 | — |
| 0.05% Naringin | 600.43 ± 52.03 | 18 |
| 0.05% Hesperidin | 615.30 ± 42.10 | 16 |
| 0.05% Rutin | 580.50 ± 42.10 | 21 |

As can be seen from Table III, the blood glucose levels in the naringin, hesperidin and rutin groups are lower than that of the control group by 18%, 16% and 21%, respectively.

EXAMPLE 3

Oral Administration of Bioflavonoids to Human

Three men in their fifties were treated with daily oral doses of 5 mg/kg, 10 mg/kg and 5 mg/kg of naringin, hesperidin and rutin, respectively, for 2 months. The blood glucose level was determined before and after the administration.

The result is shown in Table IV.

TABLE IV

| | Glucose Level (mg/dl) | | |
| --- | --- | --- | --- |
| Group | Before Administration | After 2 months | % Decrease |
| Naringin | 218 | 180 | 17 |
| Hesperidin | 150 | 110 | 23 |
| Rutin | 150 | 100 | 33 |

EXAMPLE 4

Blood Glucose Level Lowering Agent

Hard gelatin capsules were prepared using the following ingredients:

| | Quantity (mg/capsule) |
| --- | --- |
| Active ingredient (bioflavonoid) | 200 |
| Vitamin C | 50 |
| Lactose (carrier) | 150 |
| Total | 400 mg |

EXAMPLE 5

Foods Containing Bioflavonoid (1) Preparation of Tomato Ketchup and Sauce

Naringin was added to a tomato ketchup or sauce in an amount ranging from 0.01. to 50 wt % to obtain a health-improving tomato ketchup or sauce.

(2) Preparation of Wheat Flour Foods

Rutin was added to a wheat flour in an amount ranging from 0.01 to 50 wt % and breads, cakes, cookies, crackers and noodles were prepared by using the mixture to obtain health-improving foods.

(3) Preparation of Soups and Gravies

Quercetin was added-to soups and gravies in an amount ranging from 0.01 to 50 wt % to obtain health-improving soups and gravies.

(4) Preparation of Ground Beef

Diosmin was added to ground beef in an amount ranging from 0.01 to 50 wt % to obtain a health-improving ground beef.

(5) Preparation of Dairy Product

Rutin or quercetin were added to milk in an amount ranging from 0.01 to 50 wt % and various dairy products such as butter and ice cream were prepared by using the milk.

However, in case of cheese preparation, rutin or quercetin was added to the coagulated milk protein; and, in case of yogurt preparation, rutin or quercetin was added to the coagulated milk protein obtained after the fermentation.

EXAMPLE 6

Beverages Containing Bioflavonoid (1) Preparation of Vegetable Juice 200 to 1,000 mg of hesperidin was added to 1,000 ml of a tomato or carrot juice to obtain a health-improving vegetable juice.

(2) Preparation of Fruit Juice 200 to 1,000 mg of hesperidin was added to 1,000 ml of an apple or grape juice to obtain a health-improving fruit juice.

(3) Preparation of Carbonated Drink 200 to 1,000 mg of hesperidin was added to 1,000 ml of Coca-Cola® or Pepsi-Cola® to obtain a health-improving carbonated drink.

EXAMPLE 7

Health Foods Containing Bioflavonoids (1) A Health Food was Prepared by Mixing the Following Ingredients and Tableting the Mixture.

| | Quantity (wt/wt %) |
| --- | --- |
| naringin, hesperidin | 200 |
| Ginseng powder or extract | 20 |
| Sweetener and flavor | 75 |
| Total | 100 mg |

(2) Preparation of Buckwheat Powder and Extraction of Rutin from Buckwheat

Buckwheat seeds, leaves, stems and flowers were dried at a room temperature and then powdered.

Alternatively, 100 g each of buckwheat leaves and flowers was extracted twice with 200 ml each of 70% ethanol at 40° C. for 5 hours. The extracts thus obtained were filtered. The resulting extracts had 1.8% and 4% of rutin, respectively.

In addition, $Ca(OH)_2$ was added to buckwheat leaves or flowers to pH 12.0 and the mixture was allowed to stand overnight. The mixture was adjusted to pH 6 to 7 and the resulting precipitate was recovered to obtain a crude rutin (purity: 40 to 50%).

A medicine or health food containing the rutin powder or extract thus obtained may be prepared in accordance with a conventional method.

(3) A Mixture Containing the Following Ingredients was Prepared:

| | Quantity (wt/wt %) |
|---|---|
| Onion powder | 40 |
| Garlic powder | 10 |
| Jujube powder | 30 |
| Buckwheat flower powder | 5 |
| Dry grape powder | 15 |
| Total | 100 |

While the invention has been described with respect to the above specific embodiments, it should be recognized that various modifications and changes may be made to the invention by those skilled in the art which also fall within the scope of the invention as defined by the appended claims.

What is claimed is:

1. A method for lowering the blood glucose level in a mammal which comprises administering an effective amount of a bioflavonoid selected from the group consisting of hesperetin, naringenin and a mixture thereof or a plant extract containing same

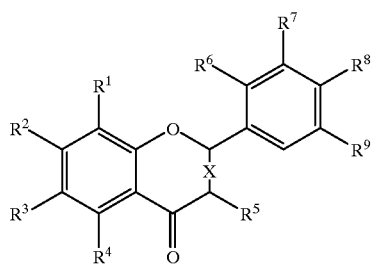

(I)

wherein $R^1$, $R^2$, $R^3$, $R^4$, $R^5$, $R^6$, $R^7$, $R^8$ and $R^9$ are each independently hydrogen; a hydroxy group; a $C_{1-9}$ alkoxy group optionally substituted with one or more substituents selected from the group consisting of a hydroxy, $C_{1-5}$ alkoxy, aryloxy, and phenyl group substituted with 1 to 3 substituents selected from the group consisting of a hydroxy, alkoxy, aryloxy, halogen, nitro and amido group; a $C_{5-9}$ cycloalkyloxy group substituted with 1 to 3 substituents selected from the group consisting of a hydroxy, alkoxy, aryloxy, halogen, nitro and amido group; a $C_{5-9}$ cycloalkylcarbonyloxy group substituted with 1 to 3 substituents selected from the group consisting or a hydroxy, alkoxy, aryloxy, halogen, nitro and amido group; a $C_{2-10}$ or $C_{16-18}$ acyloxy group optionally substituted with one or more substituents selected from the group consisting of a hydroxy, $C_{1-5}$ alkoxy, aryloxy, and phenyl group substituted with 1 to 3 substituents selected from the group consisting of a hydroxy, alkoxy, aryloxy, halogen, nitro group; a rutinosyl group; or a rhaminosyl group; and X is a single or double bond to the mammal.

2. The method of claim 1, wherein the mammal is human.

3. The method of claim 2, wherein the effective amount of the bioflavonoid ranges from 0.1 to 500 mg/kg body weight/day.

4. The method of claim 1, wherein the plant extract is a vegetable or fruit extract.

5. The method of claim 4, wherein the vegetable extract is an extract of buckwheat sprout, seeds, stems, leaves or flowers.

6. The method of claim 1, wherein the bioflavonoid or plant extract is administered in the form of a pharmaceutical composition.

7. The method of claim 1, wherein the bioflavonoid or plant extract is administered in the form of an additive or a dietary supplement in food or beverage.

8. The method of claim 7, wherein the content of the bioflavonoid in the food ranges from 0.01 to 50% by weight.

9. The method of claim 7, wherein the content of the bioflavonoid in the beverage ranges from 200 to 1,000 mg per 1,000 ml of the beverage.

* * * * *